(12) United States Patent
Fujita et al.

(10) Patent No.: US 8,921,292 B2
(45) Date of Patent: Dec. 30, 2014

(54) SHAMPOO COMPOSITION

(75) Inventors: Hiroya Fujita, Hyogo (JP); Tomoki Iwata, Hyogo (JP)

(73) Assignee: NOF Corporation, Tokyo (JP)

( * ) Notice: Subject to any disclaimer, the term of this patent is extended or adjusted under 35 U.S.C. 154(b) by 0 days.

(21) Appl. No.: 14/345,115

(22) PCT Filed: Sep. 12, 2012

(86) PCT No.: PCT/JP2012/073271
§ 371 (c)(1),
(2), (4) Date: Mar. 14, 2014

(87) PCT Pub. No.: WO2013/039086
PCT Pub. Date: Mar. 21, 2013

(65) Prior Publication Data
US 2014/0342967 A1 Nov. 20, 2014

(30) Foreign Application Priority Data
Sep. 16, 2011 (JP) .................. 2011-203812

(51) Int. Cl.
C11D 1/02 (2006.01)
C11D 1/94 (2006.01)
C11D 3/26 (2006.01)
C11D 3/37 (2006.01)
A61K 8/46 (2006.01)
A61Q 5/02 (2006.01)
A61K 8/44 (2006.01)

(52) U.S. Cl.
CPC . *A61K 8/466* (2013.01); *A61Q 5/02* (2013.01); *A61K 8/44* (2013.01); *A61K 2800/59* (2013.01)
USPC .......... 510/125; 510/126; 510/127; 510/130; 510/136; 510/137; 510/138; 510/501; 510/504

(58) Field of Classification Search
CPC .............. C11D 1/02; C11D 1/88; C11D 1/94; C11D 3/26; C11D 3/37
USPC ......... 510/125, 126, 127, 130, 136, 137, 138; 424/70.11, 70.21, 70.24
See application file for complete search history.

(56) References Cited

U.S. PATENT DOCUMENTS

| | | | | |
|---|---|---|---|---|
| 5,100,655 | A | * | 3/1992 | Takano et al. .................. 424/63 |
| 5,328,630 | A | * | 7/1994 | Nozaki et al. ................. 510/427 |
| 5,417,875 | A | * | 5/1995 | Nozaki .......................... 510/386 |
| 5,529,712 | A | * | 6/1996 | Sano et al. .................... 510/481 |
| 2001/0021691 | A1 | * | 9/2001 | Miyahara et al. ............. 510/136 |

FOREIGN PATENT DOCUMENTS

| | | |
|---|---|---|
| JP | 10-245323 A | 9/1998 |
| JP | 2002-29939 A | 1/2002 |
| JP | 2005-154286 A | 6/2005 |
| JP | 2007-217348 A | 8/2007 |
| JP | 4644493 B2 | 3/2011 |

* cited by examiner

*Primary Examiner* — Gregory R Delcotto
(74) *Attorney, Agent, or Firm* — Muncy, Geissler, Olds & Lowe, P.C.

(57) ABSTRACT

This shampoo composition includes 3 to 30 mass % of a taurine salt component (a) of an acylmethyl-β-alanine represented by formula (1);
3 to 30 mass % of an amphoteric surfactant component (b) represented by formula (2) or formula (3);
0.03 to 3 mass % of a cationized polymer component (c); and 37 to 94 mass % of a water component (d),
the mass ratio (a)/(b) of the component (a) and the component (b) is 0.2 to 3.

Chem. 1

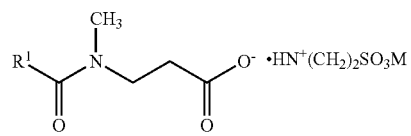

(1)

($R^1$CO represents a C8-22 acyl group. M represents an alkali metal, alkanolamine or basic amino acid.)

Chem. 2

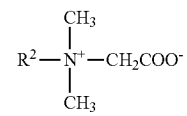

(2)

($R^2$ represents a C8-22 alkyl group or alkenyl group.)

Chem. 3

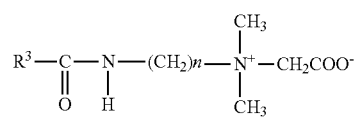

(3)

($R^3$CO represents a C8-22 acyl group, and n represents 1 to 3.)

1 Claim, No Drawings

SHAMPOO COMPOSITION

BACKGROUND OF THE INVENTION

1. Field of the Invention

The present invention relates to a shampoo composition.

2. Description of the Related Art

When hair is washed with a shampoo composition and then rinsed, hair often becomes tangled, causing split ends and trichoschisis. Also, as oil is excessively removed from hair, moist feeling is lost after drying the hair and the hair often becomes brittle. Thus, a shampoo composition has to be a cleanser composition with adequate detergency, and the composition needs to have not only foaming, foam creaminess, and detergency but also finger combability during rinsing. As for scalp care, a recent requirement is to provide a fresh feeling to a scalp after shampooing. Moreover, not only fresh scalp feeling but also moist hair feeling is being required after drying.

For example, in Patent Literature 1, described is a hair cleansing composition with improved texture during rinsing by combining N-lauroyl-N-methyl-β-alanine sodium having adequate detergency, lauramidopropyl betaine, and propylene glycol. However, although this hair cleansing composition has excellent foaming and foam creaminess, its finger combability during rinsing is dissatisfying. Also, moist hair feeling is insufficient after drying, and there is no fresh scalp feeling after drying.

Additionally, in order to add finger combability during rinsing and moist feeling after drying, Patent Literature 2 describes a cleaning composition containing N-coconut oil fatty acid acyl glutamic acid sodium glycine in which counter ions are sodium glycine. However, although this hair cleaning composition has excellent finger combability during rinsing, moist hair feeling is insignificant and there is no fresh scalp feeling after drying.

On the other hand, in order to impart conditioning effects to hair during rinsing, commonly blended is a cationized polymer (such as cationized cellulose, cationized guar gum, cationized fenugreek gum, cationized tara gum, and cationized roast bean gum). Generally, as a cationized polymer and an anionic surfactant interact electrically, a hydrophobic molecular aggregate is formed, thereby coating hair during rinsing and thus improving finger combability. For example, in Patent Literature 3, described is a shampoo composition that contains N-acyl-glutamic acid triethanolamine, an amphoteric surfactant, a polyoxyethylene alkyl diether, and a cationized polymer. However, although this shampoo composition shows improvement in finger combability during rinsing, moist hair feeling is insignificant and there is also no fresh scalp feeling after drying.

CITATION LIST

Patent Literature

[PTL 1] Japanese Unexamined Patent Application Publication No. H10-245323
[PTL 2] Japanese Patent No. 4644493
[PTL 3] Japanese Unexamined Patent Application Publication No. 2002-029939

SUMMARY OF THE INVENTION

Technical Problem

An object of the present invention is to provide a shampoo composition that has excellent foaming, foam creaminess, and finger combability during rinsing, adds moisture to hair as well as a fresh feeling to a scalp after drying, and has an excellent temporal stability.

Solution to Problem

In order to solve the problems above, the inventors, after intensive investigation, found that the above-noted object may be achieved by blending a certain taurine salt of an acylmethyl-β-alanine, an amphoteric surfactant, and a cationized polymer at a certain ratio, thus completing the present invention.

That is, the present invention is a shampoo composition that contains 3 to 30 mass % of a taurine salt component (a) of an acylmethyl-β-alanine represented by formula (1), 3 to 30 mass % of an amphoteric surfactant component (b) represented by formula (2) or formula (3), 0.03 to 3 mass % of a cationized polymer component (c), and 37 to 94 mass % of a water component (d), and in which the mass ratio (a)/(b) of the component (a) and the component (b) is 0.2 to 3. The total of the above-noted components (a) to (d) is 100 mass %.

Chem. 1

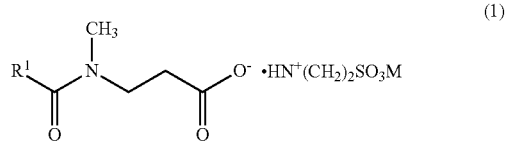

wherein $R^1CO$ represents a C8-22 acyl group, and M represents an alkali metal, alkanolamine, or basic amino acid;

Chem. 2

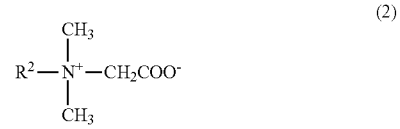

wherein $R^2$ represents a C8-22 alkyl group or alkenyl group; and

Chem. 3

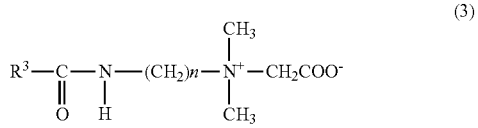

wherein $R^3CO$ represents a C8-22 acyl group, and n represents 1 to 3.

Advantageous Effects of Invention

According to the present invention, there provided is a shampoo composition that has excellent foaming, foam creaminess, and finger combability during rinsing, adds moisture to hair as well as a fresh feeling to a scalp after drying, and also has an excellent temporal stability.

DETAILED DESCRIPTION OF THE PREFERRED EMBODIMENTS

An embodiment of the present invention will be explained below.

The shampoo composition of the present invention contains a taurine salt component (a) of an acylmethyl-β-alanine, an amphoteric surfactant component (b), a cationized polymer component (c), and a water component (d) at a specific ratio. Hereinafter, each component will be explained.

[Component (a): taurine salt of an acylmethyl-β-alanine]

The component (a) for use in the present invention is a taurine salt of an acylmethyl-β-alanine represented by formula (1). $R^1CO$ in the formula represents a C8-22 acyl group, for example, a lauroyl group, a myristoyl group, a palmitoyl group, a stearoyl group, and an oleoyl group. Also, an acyl group derived from mixed fatty acid may be used. The mixed fatty acid includes a coconut oil fatty acid and a palm kernel oil fatty acid, for example. The acyl group preferably includes a lauroyl group, a myristoyl group, a coconut oil fatty acid acyl group, and a palm kernel oil fatty acid acyl group, for example. More preferably, included are a lauroyl group, a coconut oil fatty acid acyl group, and a palm kernel oil fatty acid acyl group. When the carbon number of $R^1CO$ is 7 or less, foam creaminess decreases. When the carbon number of $R^1CO$ is 23 or more, foaming decreases.

M in the formula (1) indicates an alkali metal, alkanolamine, or basic amino acid, for example, sodium, potassium, monoethanol ammonium, diethanol ammonium, triethanol ammonium, arginine, and lysine hydrochloride.

The taurine salt of an acylmethyl-β-alanine represented by formula (1) may be obtained by the method below, for example. In the coexistence of alkali, preferably, in the coexistence of sodium hydroxide, N-methyl alanine sodium is acylated by fatty acid chloride, thus preparing an acylmethyl-β-alanine sodium aqueous solution. This acylmethyl-β-alanine sodium aqueous solution contains sodium chloride. In order to remove this, pH is adjusted to 1 to 2 with acid such as sulfuric acid, so that acylmethyl-β-alanine as an oil layer and a water layer are separated for refining.

To this acylmethyl-β-alanine, it is preferable to add taurine salt which will become intended counter ions, by 1.0 to 1.2 times with respect to the mole number of acylmethyl-β-alanine, and the temperature during stirring is preferably 50 to 80° C. The taurine salt aqueous solution of an acylmethyl-β-alanine represented by formula (1) that is prepared by this method, has a pH of 6 to 8.

In the composition of the present invention, the component (a) is normally blended at 3 to 30 mass %, preferably 5 to 20 mass %. When the component (a) is blended at less than 3 mass %, foaming is likely to become poor. When the component (a) is blended at more than 30 mass %, temporal stability becomes troublesome.

[Component (b): Amphoteric Surfactant]

The component (b) for use in the present invention is an amphoteric surfactant represented by formula (2) or formula (3), in other words, a betaine type amphoteric surfactant. $R^2$ in formula (2) represents a C8-22 alkyl group or alkenyl group, for example, a lauryl group, a myristyl group, a palmityl group, a stearyl group, and an oleyl group. Also, an alkyl group or an alkenyl group derived from mixed fat may be used. For example, a coconut oil alkyl group, a palm kernel oil alkyl group, and a beef tallow alkyl group are included. Preferably, the group is a lauryl group, a myristyl group, a coconut oil alkyl group, and a palm kernel oil alkyl group. When the carbon number of $R^2$ is 7 or less, foamability decreases. When the carbon number of $R^2$ is 23 or more, foamability and temporal stability decrease.

Additionally, $R^3CO$ in formula (3) represents a C8-22 acyl group, for example, a lauroyl group, a myristoyl group, a palmitoyl group, a stearoyl group, and an oleoyl group. Also, an acyl group derived from mixed fatty acid may be used. The mixed fatty acid includes a coconut oil fatty acid and a palm kernel oil fatty acid, for example. The acyl group preferably includes a lauroyl group, a myristoyl group, a coconut oil fatty acid acyl group, and a palm kernel oil fatty acid acyl group, for example. More preferably, included are a lauroyl group, a coconut oil fatty acid acyl group, and a palm kernel oil fatty acid acyl group. When the carbon number of $R^3CO$ is 7 or less, foamability decreases. When the carbon number of $R^3CO$ is 23 or more, foamability and temporal stability decrease. Additionally, n in formula (3) indicates an integer of 1 to 3.

In the composition of the present invention, the component (b) is normally blended at 3 to 30 mass %, preferably 5 to 20 mass %. When the component (b) is blended at less than 3 mass %, foaming and foam creaminess are likely to decrease. When the component (b) is blended at more than 30 mass %, temporal stability becomes troublesome. Moreover, in case of using the amphoteric surfactant represented by formula (2) together with the amphoteric surfactant represented by formula (3), it is acceptable as long as the total blending amount of both surfactants is within the above-noted range.

[Component (c): Cationized Polymer]

The component (c) for use in the present invention is a cationized polymer, for example, a highly polymerized compound having a cationic quaternary nitrogen-containing group. A usable cationized polymer may be the one that is regularly used for a cosmetic material and can impart conditioning effects to hair. Included are, for example, cationized cellulose, cationized guar gum, and acrylic cationized polymer. The cationized cellulose includes a quaternary nitrogen-containing cellulose ether derivative represented specifically by Polymer-JR-125, Polymer-JR-400, Polymer-JR-30M, Polymer-LR-400 (any of which is manufactured by Union Carbide Corporation), Jellner-QH-300 (manufactured by Daicel Chemical Industries, Ltd.), etc. The cationized guar gum includes a quaternary nitrogen-containing guar gum derivative represented specifically by Catinal CG-100, Catinal CG-100S (any of which is manufactured by Toho Chemical Industry Co., Ltd.), Cosmedia C-261 (manufactured by Henkel Corporation), etc. The acrylic cationized polymer includes a dimethyldiallylammonium chloride derivative represented specifically by Marcoat 100, Marcoat 280, and Marcoat 550 (any of which is manufactured by Merck Ltd.), Cellcoat H-100 and Cellcoat L-200 (any of which is manufactured by National Starch and Chemical Co.), etc. As the component (c), one or two or more kinds of cationized polymers may be used.

In the composition of the present invention, the component (c) is normally blended at 0.03 to 3 mass %, preferably 0.05 to 2 mass %, more preferably 0.1 to 1.5 mass %. At less than 0.03 mass %, finger combability during washing and rinsing is likely to decrease. At more than 3 mass %, not only does temporal stability becomes a problem but also viscosity increases, so that manufacture becomes difficult.

[(d) water]

The component (d) in the present invention is water and is normally blended at 37 to 94 mass %, preferably 60 to 90 mass %.

In the composition of the present invention, the mass ratio (a)/(b) of the component (a) and the component (b) is normally 0.2 to 3, preferably 0.5 to 2.5, more preferably 0.8 to 2. When the mass ratio (a)/(b) is less than 0.2, finger combability during rinsing becomes poor, and moist hair feeling after drying and fresh scalp feeling after drying decrease. When the mass ratio (a)/(b) exceeds 3, finger combability during rinsing deteriorates and moist hair feeling becomes poor after drying.

[Shampoo Composition]

The shampoo composition of the present invention is provided by mixing the above-noted components (a) to (d). Other useful shampoo components may be properly added to the shampoo composition of the present invention within the limits of maintaining the effect of the present invention.

As such a component, included are, for example, an amphoteric surfactant, except for the component (b), such as an imidazolinium betaine-based amphoteric surfactant and a sulfobetaine-based amphoteric surfactant; a nonionic surfactant such as a higher fatty acid alkanolamide-based nonionic surfactant, amine oxide-based nonionic surfactant, and polyoxyethylene alkyl ether-based nonionic surfactant; a cationic surfactant such as an alkyltrimethylammonium chloride and dialkyldimethylammonium chloride; a foaming enhancer such as a higher fatty acid and higher alcohol; a pearl gloss-imparting agent such as an ethylene glycol distearate and triethylene glycol distearate; a thickener such as methyl cellulose, hydroxypropylmethyl cellulose, carboxyvinyl polymer, and xanthan gum; a moisturizing agent such as 1,3-butylene glycol, propylene glycol, dipropylene glycol, glycerol, diglycerol, isoprene glycol, and hydrolyzed protein liquid; oil such as squalane, jojoba oil, olive oil, castor oil, lanolin, and lecithin; a silicone derivative such as a highly polymerized methylpolysiloxane and dimethylsiloxane-methyl(polyoxyethylene)siloxane copolymer; a preservative such as paraben; a disinfectant such as salicylic acid, isopropyl methylphenol, triclosan, zinc pyrithione, and piroctone olamine; a pH regulator such as citric acid and sodium citrate; a sequestering agent such as edetate and hydroxyethane diphosphonic acid; an ultraviolet light absorber such as 2-ethylhexyl p-methoxycinnamate, oxybenzone, and 2-ethylhexyl p-dimethylaminobenzoate, tonic such as 5-methyl-2-isopropyl cyclohexanol and capsicum tincture; an antioxidant such as dibutylhydroxytoluene and tocopherol acetate; an animal and plant-derived extract; a pigment; and perfume.

EXAMPLES

The present invention will be explained below in further detail by referring to examples and comparative examples. As Examples 1 to 8 and Comparative Examples 1 to 12, shampoo compositions shown in Table 1 and Table 2 were prepared and evaluated in the following methods.

(1) Quality of Foam During Shampooing

As panelists, ten males and ten females each used 5 g of the shampoo compositions and evaluated foaming and foam creaminess when they washed their hair and scalp therewith. Evaluation was made in the following three grades based on the total points of twenty panelists, with 2 points for good foaming and foam creaminess, 1 point for fair foaming and foam creaminess, and 0 points for poor foaming and foam creaminess.

◯: Good quality of foam (total of 30 points or above)

Δ: Fair quality of foam (total of 20 points or above and less than 30 points)

x: Poor quality of foam (total of less than 20 points)

(2) Finger Combability During Rinsing

As panelists, ten males and ten females each used 5 g of the shampoo compositions and evaluated finger combability during rinsing after they washed their hair and scalp therewith. Evaluation was made in the following three grades based on the total points of twenty panelists, with 2 points for no squeaky feeling, 1 point for a slightly squeaky feeling, and 0 points for a strong squeaky feeling.

◯: Good finger combability (total of 30 points or above)

Δ: Fair finger combability (total of 20 points or above and less than 30 points)

x: Poor finger combability (total of less than 20 points)

(3) Moist Hair Feeling after Drying

As panelists, ten males and ten females each used 5 g of the shampoo compositions and evaluated moist hair feeling based on combability after washing, rinsing and air-drying their hair. Evaluation was made in the following three grades based on the total point of twenty panelists, with 2 points for no squeaky feeling of the hair and smooth combability, 1 point for slightly smooth combability, and 0 points for a squeaky feeling of the hair and poor combability.

◯: Good moist hair feeling after drying (total of 30 points or above)

Δ: Fair moist hair feeling after drying (total of 20 points or above and less than 30 points)

x: Poor moist hair feeling after drying (total of less than 20 points)

(4) Fresh Scalp Feeling after Drying

As panelists, ten males and ten feniales each used 5 g of the shampoo compositions and evaluated fresh scalp feeling after washing, rinsing and air-drying their hair. Evaluation was made based on the total points of twenty panelists, with 2 points for clean and fresh feel of a scalp, 1 point for slightly fresh feel, and 0 points for no clean and fresh feel of a scalp.

◯: Good fresh scalp feeling after drying (total of 30 points or above)

Δ: Slightly fresh scalp feeling after drying (total of 20 points or above and less than 30 points)

x: Little fresh scalp feeling after drying (total of less than 20 points)

(5) Temporal Stability

Each composition was sealed in a transparent glass container and was stored for one month at −5° C., 25° C., and 45° C., and the appearance of each was observed and evaluated in the following three grades.

⊚: Good stability (no change in appearances at any temperature)

○: Fair stability (A little solidification and separation were found at any temperature, but they returned to normal at room temperature.)

Δ: Slightly poor stability (Slight separation or coloring was found at any temperature.)

x: Poor stability (Solidification, separation, or noticeable coloring was found at any temperature)

TABLE 1

|   |   | Example | | | | | | | |
|---|---|---|---|---|---|---|---|---|---|
|   |   | 1 | 2 | 3 | 4 | 5 | 6 | 7 | 8 |
| (a) | N-lauroyl-N-methyl-β-alanine taurine sodium | 6 | — | — | 10 | — | 10 | 20 | 14 |
|  | N-coconut oil fatty acid-N-methyl-β-alanine taurine sodium | — | 10 | 4 | — | 10 | — | — | — |
|  | N-coconut oil fatty acid-N-methyl-B-alanine taurine arginine | — | — | — | — | — | — | — | — |
| (b) | Coconut oil fatty acid amidopropyldimethylaminoacetic acid betaine | 4 | — | 15 | — | 6 | 5 | 25 | 5 |
|  | Coconut oil alkyldimethylaminoacetic acid betaine | — | 18 | — | 5 | — | 5 | | |
|  | O-[2-hydroxy-3-(trimethylammonio)propyl]hydroxyethylcellulose chloride (Polymer-JR-30M: manufactured by Union Carbide Corporation) | 0.1 | — | — | — | 0.2 | 0.2 | 2.5 | 0.3 |
|  | Acrylamide-acrylic acid-dimethyldiallylammonium chloride copolymer (Marcoat 100: manufactured by Merck Co.) | — | 1 | — | 0.1 | — | 0.3 | — | — |
|  | Guar gum hydroxypropyltrimethylammonium chloride ether (Catinal CG-100: manufactured by Toho Chemical Industry Co., Ltd.) | — | — | 0.2 | 0.1 | — | 0.3 | — | — |
| (d) | Water | 89.9 | 71 | 80.8 | 84.8 | 83.8 | 79.2 | 52.5 | 80.7 |
| Evaluation item | Quality of foam during shampooing | ○ (31) | ○ (37) | ○ (34) | ○ (33) | ○ (32) | ○ (37) | ○ (33) | ○ (33) |
|  | Finger combability during rinsing- | ○ (32) | ○ (34) | ○ (35) | ○ (35) | ○ (31) | ○ (34) | ○ (30) | ○ (31) |
|  | Moist hair feeling after drying | ○ (32) | ○ (36) | ○ (31) | ○ (37) | ○ (35) | ○ (34) | ○ (34) | ○ (35) |
|  | Fresh scalp feeling after drying | ○ (30) | ○ (31) | ○ (32) | ○ (33) | ○ (33) | ○ (33) | ○ (33) | ○ (33) |
|  | Temporal stability | ⊚ | ⊚ | ⊚ | ⊚ | ⊚ | ⊚ | ⊚ | ⊚ |
|  | (a)/(b) | 1.5 | 0.6 | 0.3 | 2 | 1.7 | 1 | 0.8 | 2.8 |

TABLE 2

|   |   | Comparative Example | | | | | |
|---|---|---|---|---|---|---|---|
|   |   | 1 | 2 | 3 | 4 | 5 | 6 |
| (a) | N-lauroyl-N-methyl-β-alanine taurine sodium | — | 20 | 15 | — | 3 | 20 |
|  | N-coconut oil fatty acid-N-methyl-β-alanine taurine sodium | — | — | — | — | — | — |
|  | N-coconut oil fatty acid-N-methyl-β-alanine taurine arginine | — | — | — | 40 | — | — |
| (b) | Coconut oil fatty acid amidopropyldimethylaminoacetic acid betaine | — | — | 10 | — | — | — |
|  | Coconut oil alkyldimethylaminoacetic acid betaine | 15 | — | — | 40 | 20 | 5 |
| (c) | O-[2-hydroxy-3-(trimethylammonio)propyl]hydroxyethylcellulose chloride (Polymer-JR-30M: manufactured by Union Carbide Corporation) | 0.1 | 1 | — | 1 | — | — |
|  | Acrylamide-acrylic acid-dimethyldiallylammonium chloride copolymer (Marcoat 100: manufactured by Merck Co.) | — | — | — | — | — | 0.5 |
|  | Guar gum hydroxypropyltrimethylammonium chloride ether (Catinal CG-100, manufactured by Toho Chemical Industry Co., Ltd.) | — | — | — | — | 0.6 | — |
| Other components | N-coconut oil fatty acid acyl glutamic acid triethanolamine | — | — | — | — | — | — |
|  | N-lauroyl-N-methyl-β-alanine sodium | — | — | — | — | — | — |
|  | N-coconut oil fatty acid acyl-N-methyl-β-alanine triethanolamine | — | — | — | — | — | — |
|  | N-coconut oil fatty acid acyl glutamic acid-alanine sodium | — | — | — | — | — | — |
|  | N-coconut oil fatty acid acyl glutamic acid-alanine-N-methyltaurine sodium | — | — | — | — | — | — |
| (d) | Water | 84.9 | 79.0 | 75.0 | 19.0 | 76.4 | 74.5 |
| Evaluation item | Quality of foam during shampooing | x (10) | Δ (22) | Δ (26) | ○ (32) | Δ (28) | ○ (35) |
|  | Finger combability during rinsing | x (15) | Δ (26) | x (14) | x (19) | x (18) | Δ (26) |
|  | Moist hair feeling after drying | x (18) | Δ (20) | ○ (34) | ○ (34) | Δ (23) | Δ (27) |
|  | Fresh scalp feeling after drying | x (12) | ○ (31) | ○ (33) | ○ (33) | x (18) | ○ (33) |
|  | Temporal stability | ⊚ | ○ | ⊚ | x | ⊚ | ○ |
|  | (a)/(b) | — | — | 1.5 | 1 | 0.2 | 4 |

|   |   | Comparative Example | | | | | |
|---|---|---|---|---|---|---|---|
|   |   | 7 | 8 | 9 | 10 | 11 | 12 |
| (a) | N-lauroyl-N-methyl-β-alanine taurine sodium | 6 | — | — | — | — | — |
|  | N-coconut oil fatty acid-N-methyl-β-alanine taurine sodium | 4 | — | — | — | — | — |
|  | N-coconut oil fatty acid-N-methyl-β-alanine taurine arginine | — | — | — | — | — | — |

TABLE 2-continued

| | | | | | | | |
|---|---|---|---|---|---|---|---|
| (b) | Coconut oil fatty acid amidopropyldimethylaminoacetic acid betaine | — | — | — | — | — | — |
| | Coconut oil alkyldimethylaminoacetic acid betaine | 6 | 10 | 6 | 5 | — | 6 |
| (c) | O-[2-hydroxy-3-(trimethylammonio)propyl]hydroxyethylcellulose chloride (Polymer-JR-30M: manufactured by Union Carbide Corporation) | — | — | — | 0.1 | 0.1 | — |
| | Acrylamide-acrylic acid-dimethyldiallylammonium chloride copolymer (Marcoat 100: manufactured by Merck Co.) | 4 | 0.5 | 0.1 | — | — | 0.05 |
| | Guar gum hydroxypropyltrimethylammonium chloride ether (Catinal CG-100, manufactured by Toho Chemical Industry Co., Ltd.) | — | — | — | 0.1 | — | 0.05 |
| Other components | N-coconut oil fatty acid acyl glutamic acid triethanolamine | — | 20 | — | — | — | — |
| | N-lauroyl-N-methyl-β-alanine sodium | — | — | 12 | — | — | — |
| | N-coconut oil fatty acid acyl-N-methyl-β-alanine triethanolamine | — | — | — | 12 | — | — |
| | N-coconut oil fatty acid acyl glutamic acid-alanine sodium | — | — | — | — | 8 | — |
| | N-coconut oil fatty acid acyl glutamic acid-alanine-N-methyltaurine sodium | — | — | — | — | — | 8 |
| (d) | Water | 80.0 | 69.5 | 81.9 | 78.8 | 85.9 | 85.9 |
| Evaluation item | Quality of foam during shampooing | × (18) | Δ (21) | Δ (28) | ○ (33) | Δ (26) | Δ (28) |
| | Finger combability during rinsing | Δ (24) | Δ (27) | Δ (25) | Δ (27) | Δ (28) | ○ (31) |
| | Moist hair feeling after drying | ○ (25) | × (14) | × (15) | × (16) | Δ (29) | Δ (28) |
| | Fresh scalp feeling after drying | ○ (31) | × (18) | ○ (30) | ○ (32) | × (18) | × (19) |
| | Temporal stability | × | ○ | ◎ | ◎ | ◎ | ◎ |
| | (a)/(b) | 1.7 | — | — | — | — | — |

According to the evaluation results of Examples 1 to 8 shown in Table 1, the shampoo compositions with the components of the present invention have excellent foaming and foam creaminess as well as finger combability during rinsing, add moisture to hair and a fresh feeling to a scalp after drying, and also have an excellent temporal stability.

On the other hand, as shown in Table 2, Comparative Examples 1 to 12 did not perform well enough. Specifically, since the component (a) was not blended in Comparative Example 1, the quality of foam was inferior and finger combability during rinsing, moist hair feeling after drying and fresh scalp feeling after drying were poor. Since the component (b) was not blended in Comparative Example 2, the quality of foam, finger combability during rinsing, moist hair feeling after drying were slightly inferior to the examples. Since the component (c) was not blended in Comparative Example 3, the quality of foam was slightly inferior to the examples and finger combability during rinsing was poor. Since the component (a) and the component (b) were blended more than the upper limit specified by the present invention in Comparative Example 4, finger combability during rinsing and temporal stability were poor.

Since the mass ratio (a)/(b) was below the lower limit specified by the present invention in Comparative Example 5, the quality of foam and moist hair feeling after drying were slightly inferior to the examples, and finger comb ability during rinsing and fresh scalp feeling after drying were poor. Since the mass ratio (a)/(b) exceeded the upper limit specified by the present invention in Comparative Example 6, finger combability during rinsing and moist hair feeling after drying were slightly inferior to the examples. Since the blending quantity of the component (c) exceeded the upper limit specified by the present invention in Comparative Example 7, finger combability during rinsing was slightly inferior to the examples and the quality of foam was poor.

Since a surfactant of a glutamic acid skeleton was used instead of the component (a) of an alanine skeleton in Comparative Example 8, the quality of foam and finger combability during rinsing were slightly inferior to the examples, and moist hair feeling and fresh scalp feeling were poor after drying. Since a non-taurine salt surfactant was used instead of the component (a) in Comparative Example 9, the quality of foam and finger combability during rinsing were slightly inferior to the examples, and, moist hair feeling was poor after drying. Since a non-taurine salt surfactant was used instead of the component (a) in Comparative Example 10, finger combability during rinsing was slightly inferior to the examples, and moist hair feeling was poor after drying. Since a surfactant of a glutamic acid skeleton was used instead of the component (a) of an alanine skeleton in Comparative Example 11, the quality of foam, finger combability during rinsing and moist hair feeling after drying were slightly inferior to the examples, and fresh scalp feeling was poor after drying. Since a surfactant of a glutamic acid skeleton was used instead of the component (a) of an alanine skeleton in Comparative Example 12, the quality of foam and moist hair feeling after drying were slightly inferior to the examples, and fresh scalp feeling was poor after drying.

In addition to priority claims based on the Japanese Patent Application No. 2011-203812 filed on Sep. 16, 2011, the disclosed contents of the application are incorporated in the description.

What is claimed is:

1. A shampoo composition comprising:
   3 to 30 mass % of a taurine salt component (a) of an acylmethyl-β-alanine represented by formula (1);
   3 to 30 mass % of an amphoteric surfactant component (b) represented by formula (2) or formula (3);
   0.03 to 3 mass % of a cationized polymer component (c); and
   37 to 94 mass % of a water component (d), wherein the mass ratio (a)/(b) of the component (a) and the component (b) is 0.2 to 3:

Chem. 1
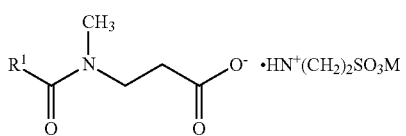
(1)
wherein $R^1CO$ represents a C8-22 acyl group, and M represents an alkali metal, alkanolamine, or basic amino acid;
Chem. 2
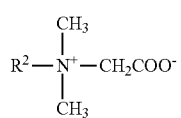
(2)
wherein $R^2$ represents a C8-22 alkyl group or alkenyl group; and
Chem. 3
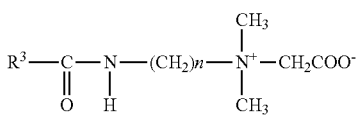
(3)
wherein $R^3CO$ represents a C8-22 acyl group, and n represents 1 to 3.
* * * * *